(12) United States Patent
Taylor

(10) Patent No.: US 9,878,136 B2
(45) Date of Patent: Jan. 30, 2018

(54) METHOD OF USING A GROOVED DILATOR AND IMPLANTING A PROSTHETIC IN A PENIS

(71) Applicant: Coloplast A/S, Humlebaek (DK)

(72) Inventor: Jeffrey Brian Taylor, Forest Lake, MN (US)

(73) Assignee: Coloplast A/S, Humlebaek (DK)

( * ) Notice: Subject to any disclaimer, the term of this patent is extended or adjusted under 35 U.S.C. 154(b) by 0 days.

(21) Appl. No.: 15/446,016

(22) Filed: Mar. 1, 2017

(65) Prior Publication Data

US 2017/0173313 A1    Jun. 22, 2017

Related U.S. Application Data

(63) Continuation of application No. 14/501,980, filed on Sep. 30, 2014, now abandoned.

(30) Foreign Application Priority Data

Sep. 28, 2015   (EP) ..................................... 15187102

(51) Int. Cl.
*A61F 2/26* (2006.01)
*A61M 29/00* (2006.01)
*A61F 5/41* (2006.01)

(52) U.S. Cl.
CPC ............... *A61M 29/00* (2013.01); *A61F 2/26* (2013.01); *A61F 5/41* (2013.01); *A61F 2005/411* (2013.01)

(58) Field of Classification Search
CPC .. A61M 29/00; A61B 17/00; A61B 17/06109; A61B 17/0469; A61B 2017/0085; A61B 2017/00805; A61B 2017/06057; A61B 2017/06085; A61B 2017/0472; A61B 2017/0608; A61F 2/26; A61F 2250/0051; A61F 2005/411
USPC .............................. 600/38–41; 606/190, 191
See application file for complete search history.

(56) References Cited

U.S. PATENT DOCUMENTS

| | | | |
|---|---|---|---|
| 3,893,456 A | 7/1975 | Small et al. | |
| 4,244,370 A | 1/1981 | Furlow et al. | |
| 4,350,151 A | 9/1982 | Scott | |
| 5,217,481 A | 6/1993 | Barbara | |
| 5,868,729 A | 2/1999 | Pelfrey | |
| 5,968,067 A | 10/1999 | Mooreville et al. | |
| 7,066,878 B2 | 6/2006 | Eid | |
| 2004/0010244 A1 | 1/2004 | George et al. | |
| 2004/0225182 A1 | 11/2004 | Eid | |
| 2007/0276370 A1 | 11/2007 | Altarac et al. | |
| 2009/0105530 A1* | 4/2009 | Kuyava ..................... | A61F 2/26 600/40 |

(Continued)

FOREIGN PATENT DOCUMENTS

CN   201668855 U   12/2010
EP   2415422 A1    2/2012

(Continued)

*Primary Examiner* — Samuel Gilbert
(74) *Attorney, Agent, or Firm* — Coloplast Corp., Coloplast A/S; Nick Baumann

(57) ABSTRACT

A method of implanting a prosthetic in a penis includes moving a dilation portion of a dilator in a distal direction and in a proximal direction within the corpora cavernosum, dilating a first portion of tissue in the corpora cavernosum, and leaving a second grooved portion of the tissue in the corpora cavernosum un-dilated and vascularized.

19 Claims, 20 Drawing Sheets

(56) References Cited

U.S. PATENT DOCUMENTS

| | | |
|---|---|---|
| 2009/0253853 A1 | 10/2009 | Lin et al. |
| 2011/0071344 A1 | 3/2011 | Morningstar et al. |
| 2011/0144427 A1 | 6/2011 | Morningstar et al. |
| 2011/0166589 A1 | 7/2011 | Morningstar |

FOREIGN PATENT DOCUMENTS

| | | |
|---|---|---|
| WO | 03071970 A1 | 9/2003 |
| WO | 2004045421 A1 | 6/2004 |

* cited by examiner

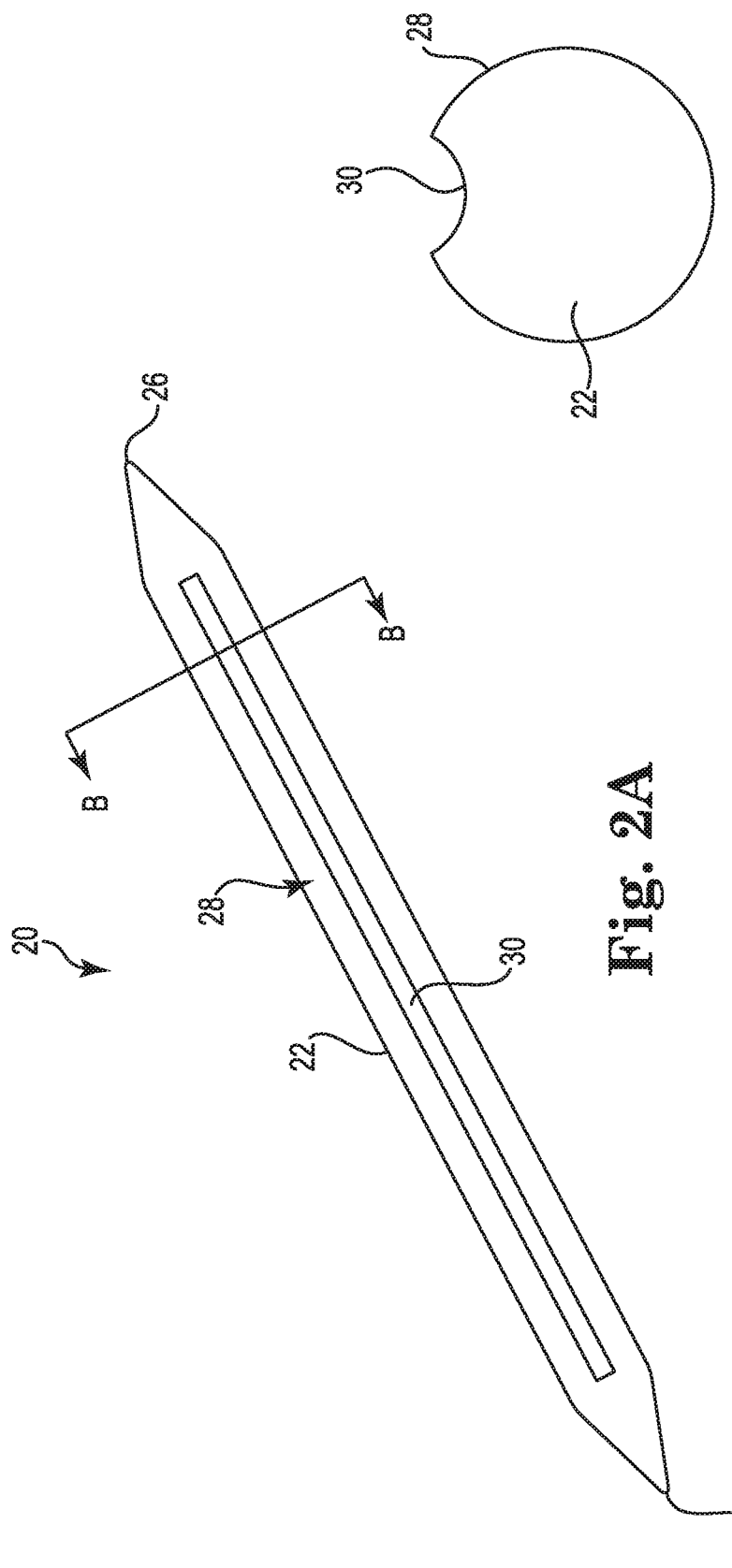

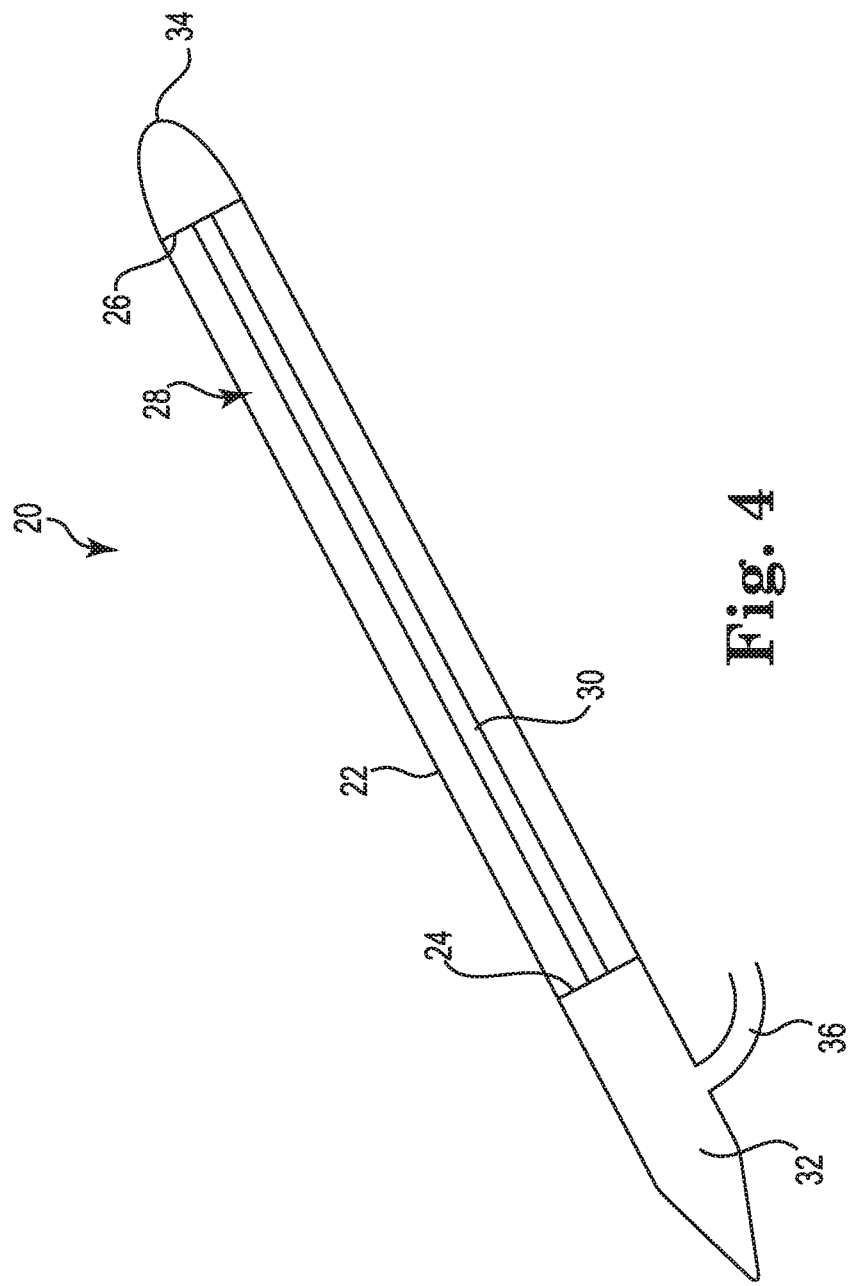

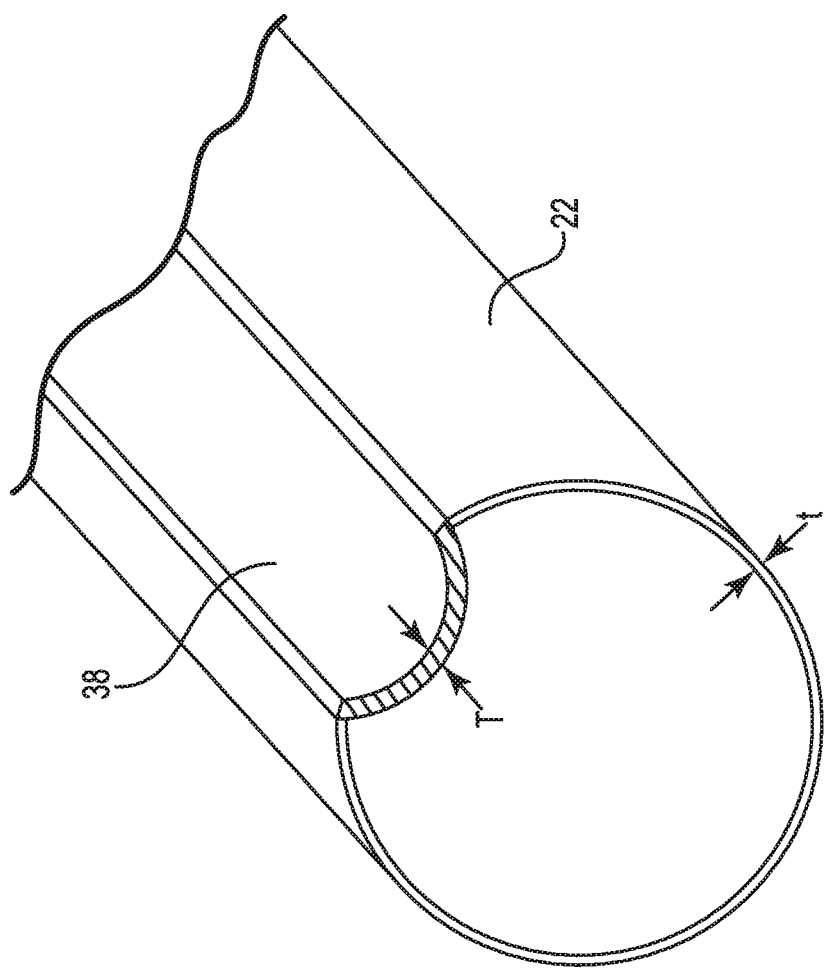

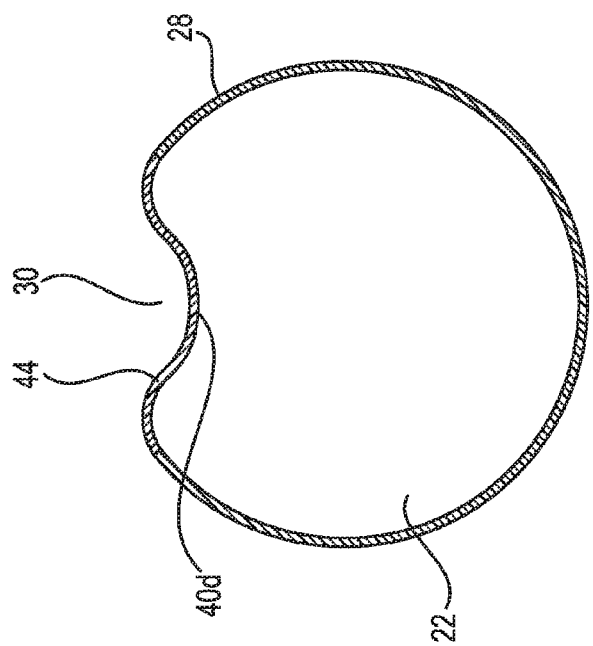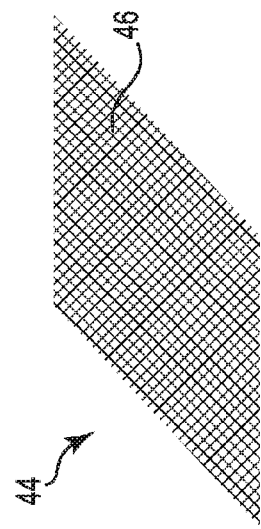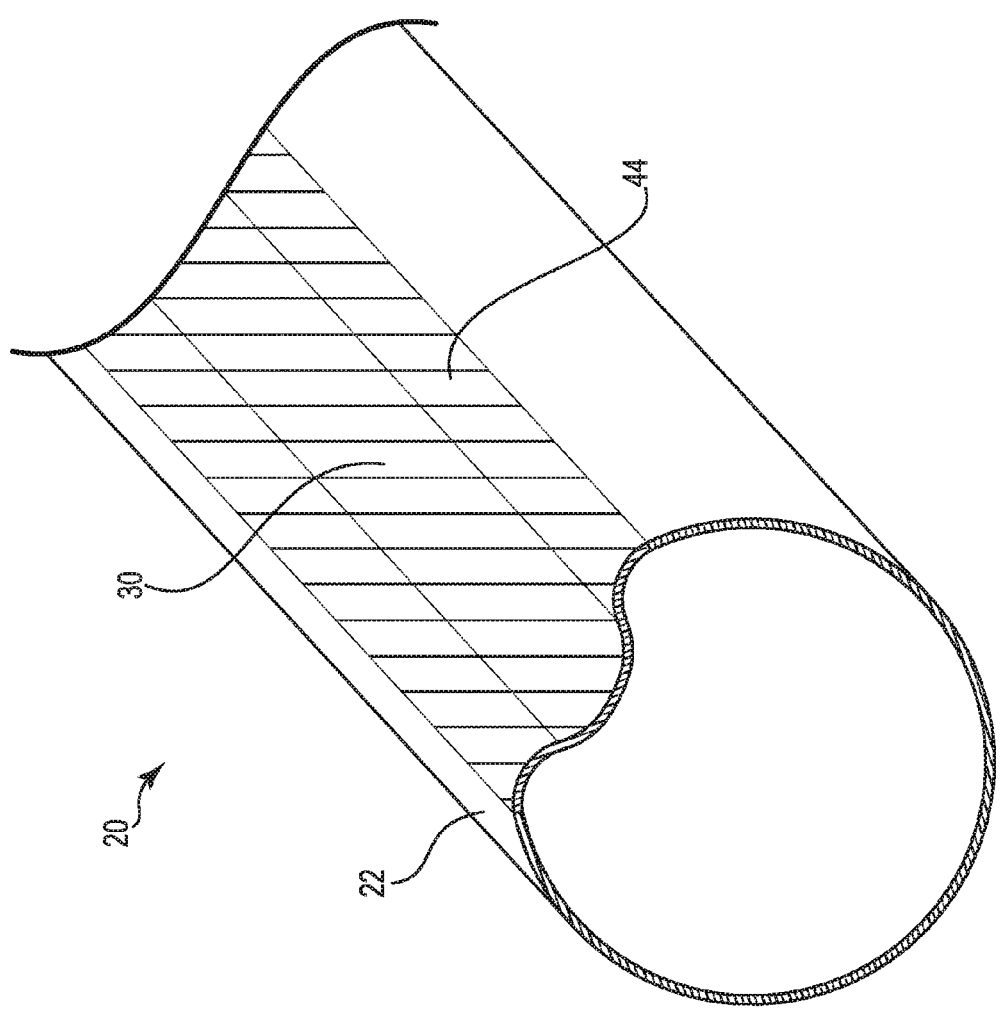

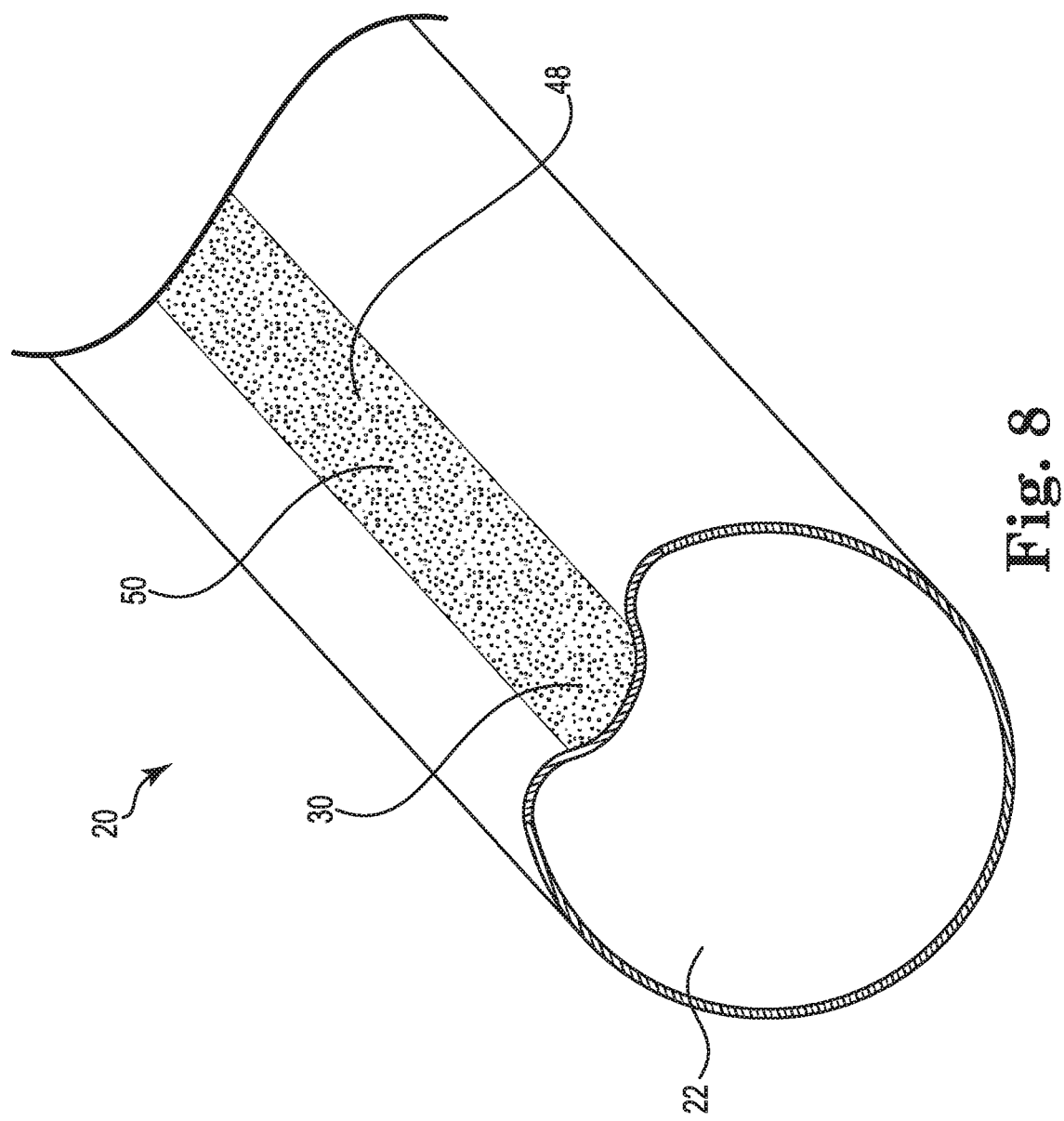

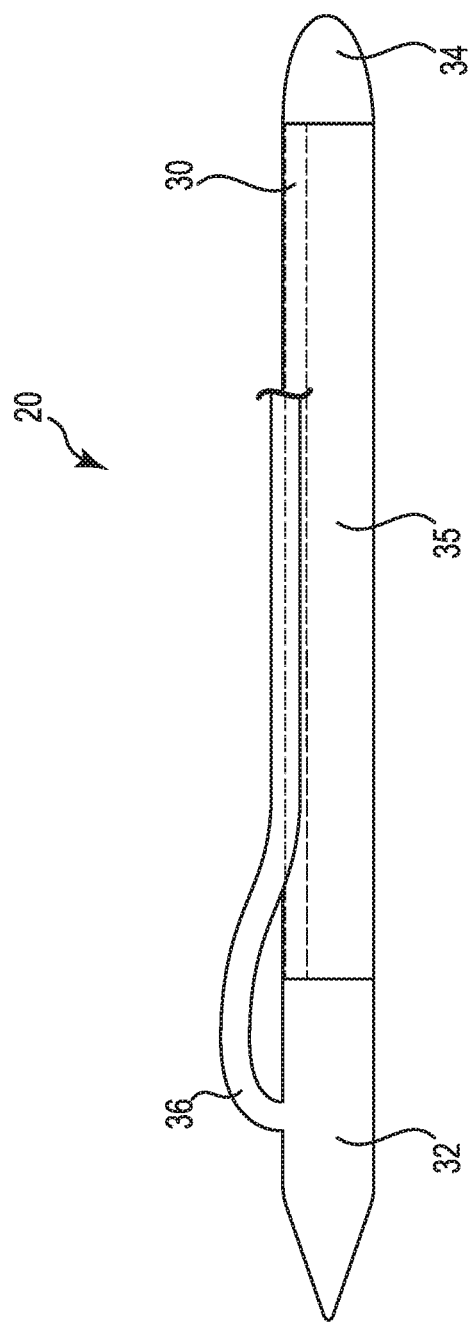

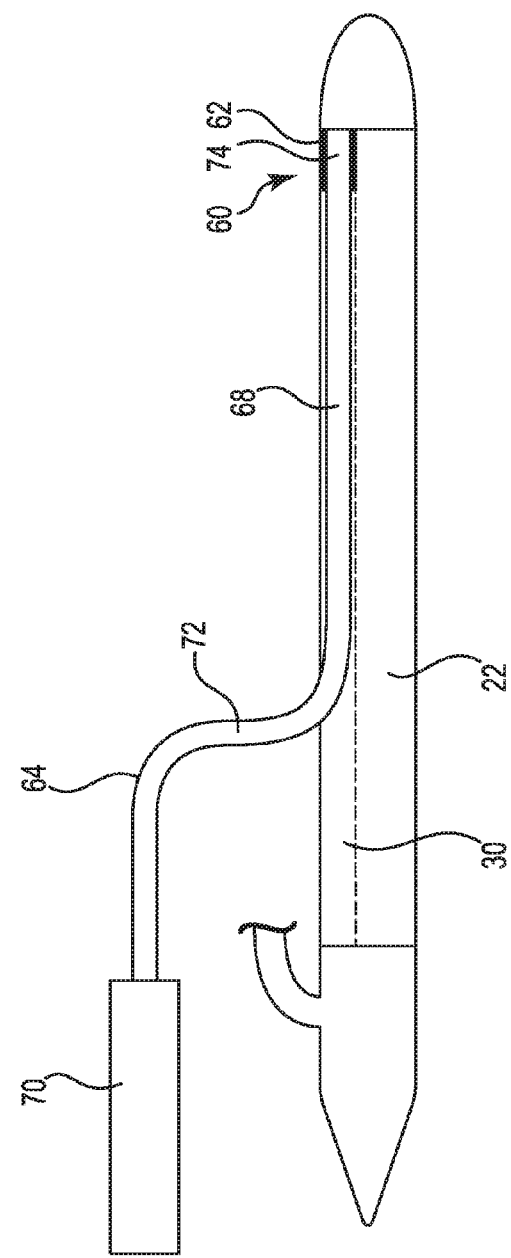
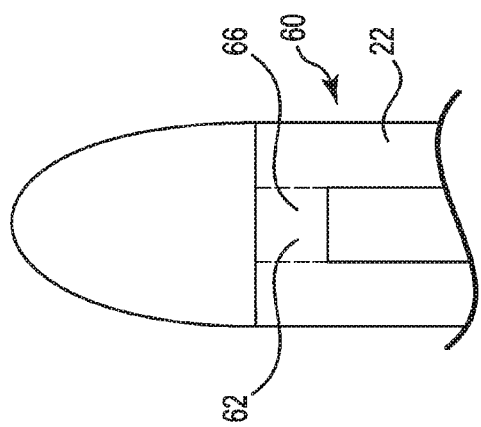
Fig. 11A
Fig. 11B

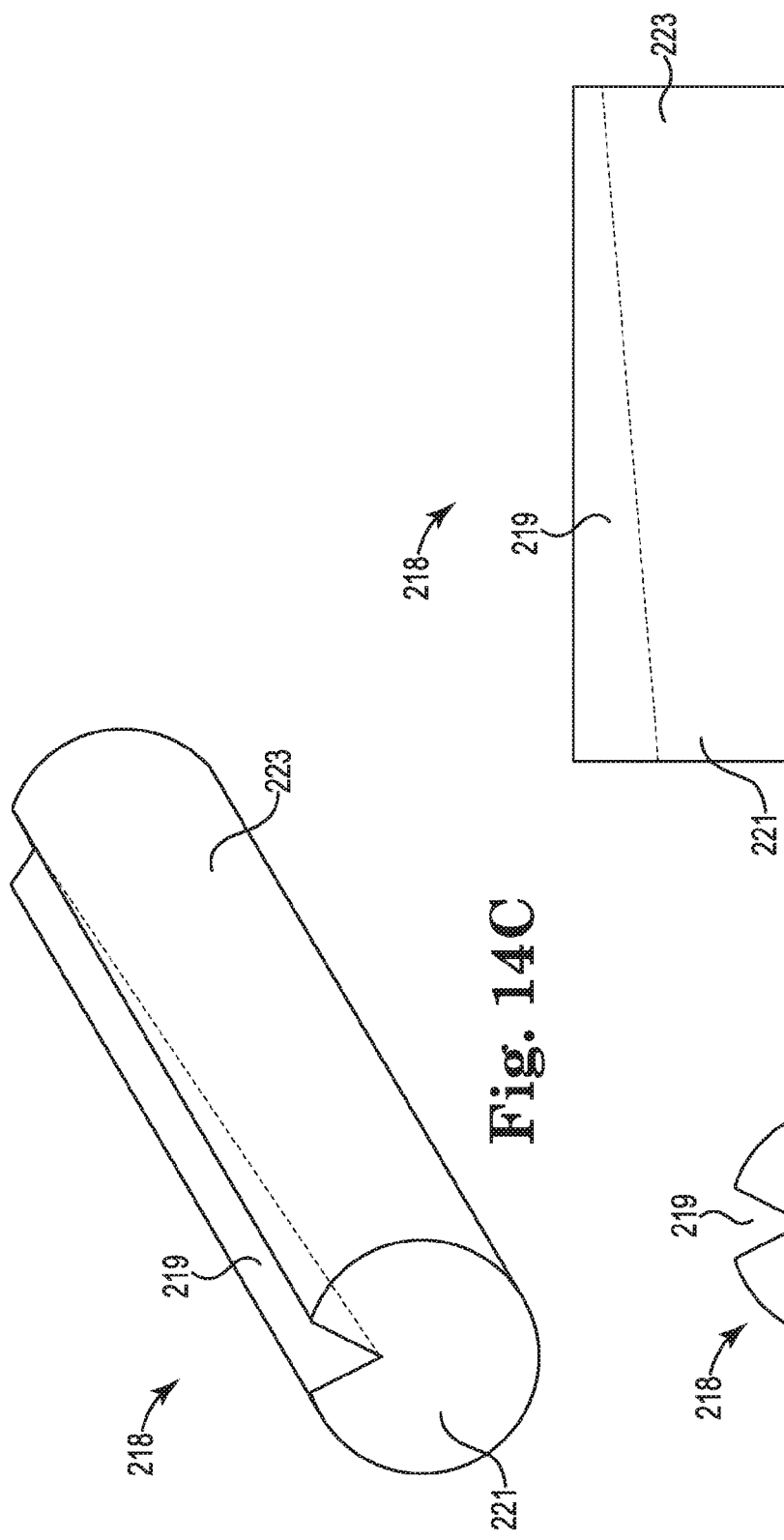

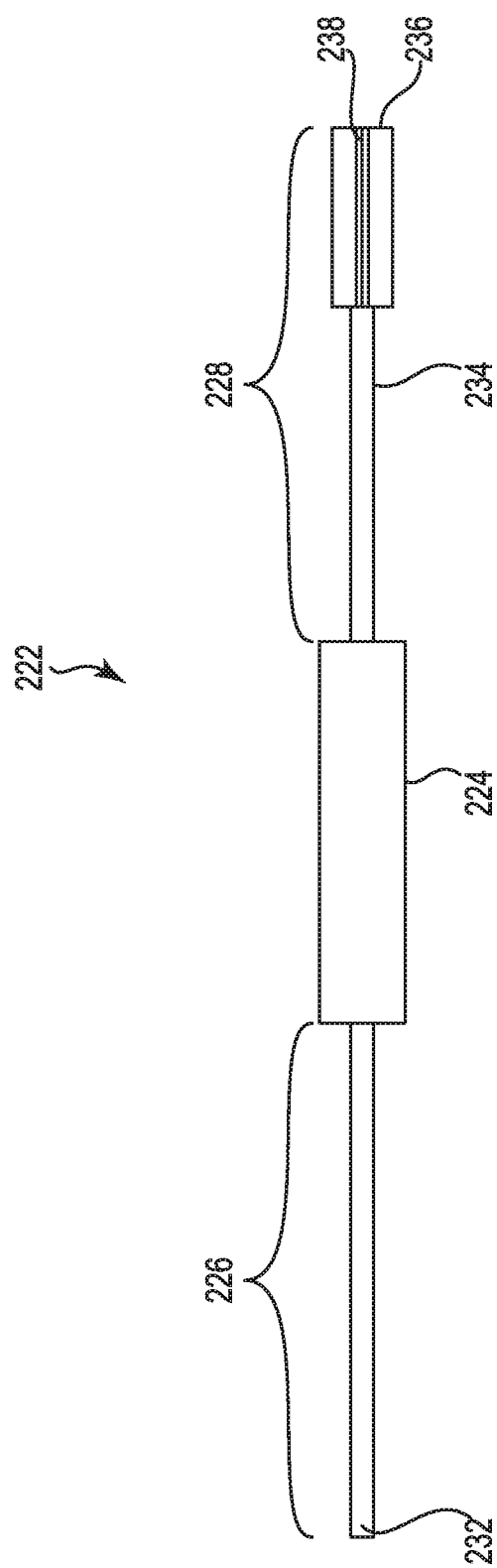

METHOD OF USING A GROOVED DILATOR AND IMPLANTING A PROSTHETIC IN A PENIS

BACKGROUND

An implanted penile prosthetic is effective in relieving erectile dysfunction in men.

A penile prosthetic typically includes a cylinder that is implanted in each corpora cavernosum of the penis as well as a fluid reservoir and pump and valve mechanisms to move fluid from the reservoir to the cylinder to create an erection in the penis. Other penile prosthetics include a malleable cylinder without inflation fluid. The erectile dysfunction condition is typically a result of reduced or no blood supply to the tissue of the corpora cavernosum leading to the sponge-like tissue of the corpora losing its expanding capability. The lack of blood supply to the corpora cavernosa may be caused by both psychological and physiological reasons and/or as a reaction to medication.

Placement of a cylinder in the corpora cavernosum in a surgical procedure includes dilating the sponge-like tissue of the corpora cavernosum with a Brooks® corporal dilator to form an implant space sized to receive the cylinder.

The above-described penile prosthetics have proven effective in relieving erectile dysfunction in men. However, improvements to penile prostheses would be welcomed by surgeons and patients alike.

SUMMARY

One aspect provides a dilator for dilating the tissue of a corpora cavernosum of a penis. The dilator includes a handle, a stem and an intermediate portion connecting the handle and the stem. A dilation portion is attached at a distal end of the stem and has a larger diameter than the stem portion. The dilation portion includes an exterior surface defining a groove having a groove depth that is configured to leave a section of tissue in the corpora cavernosum undisturbed and un-dilated to allow for vascularization of the section of tissue in aid of an erection.

One aspect provide a kit of parts including a packaging, a dilator for dilating the tissue of a corpora cavernosum of a penis, a set of instructions for use and an implantable penile prosthetic insert configured to be placed in a corpora cavernosum of a penis and to transition the penis between a flaccid and an erect state. The dilation portion includes an exterior surface defining a groove having a groove depth that is configured to leave a section of tissue in the corpora cavernosum undisturbed and un-dilated to allow for vascularization of the section of tissue in aid of an erection.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

FIG. 2A is a top view of one embodiment of a penile prosthetic insert.

FIG. 2B is a cross-sectional view of the insert of FIG. 2A taken along the line B-B in FIG. 2A.

FIG. 4 is a top view of one embodiment of a penile prosthetic insert including a rear proximal tip and a front distal tip.

FIG. 5 is a sectional perspective view of one embodiment of a penile prosthetic insert including a channel with by a wall having a greater thickness than a surrounding portion of a body of the insert.

FIG. 7A is a sectional perspective view of one embodiment of a penile prosthetic insert including a channel provided with a reinforcing layer.

FIG. 7B is a cross-sectional view of the insert of FIG. 7A.

FIG. 7C is a schematic perspective view of one embodiment of the reinforcing layer of FIG. 7A-7B.

FIG. 8 is a sectional perspective view of one embodiment of a penile prosthetic insert including a channel coated with a tissue ingrowth promoting material.

FIG. 10 is a partly cross-sectional side view of one embodiment of a penile prosthetic insert including an inflatable chamber having a channel.

FIG. 11A is a schematic side view of one embodiment of a penile prosthetic insert and an insert positioning tool engaged with the insert and partly accommodated in a channel in the insert.

FIG. 11B is a sectional top view of a distal end portion of the insert of FIG. 11A.

FIG. 14C is a perspective sectional view of a dilation portion of a dilation tool according to one embodiment.

FIG. 14D is a side view of the embodiment of the dilation portion illustrated in FIG. 14C.

FIG. 14E is a cross-sectional view of one embodiment of a dilation portion including a plurality of grooves.

FIG. 15 is a top view of one embodiment of a combined insert positioning tool and dilation tool.

DETAILED DESCRIPTION

Figure 1:
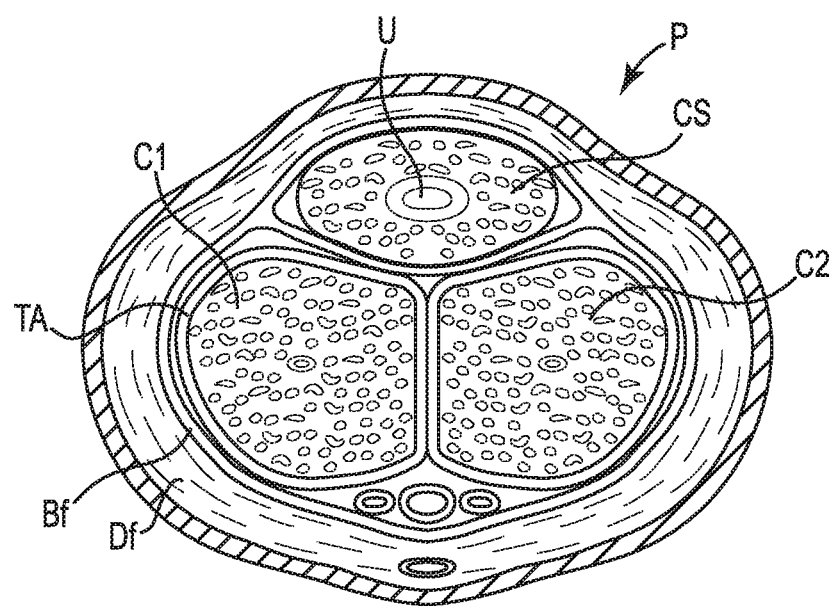
FIG. 1 is a cross-sectional view of a penis P reclined against the abdomen in an orientation positioned for access by a surgeon.

In the following Detailed Description, reference is made to the accompanying drawings, which form a part hereof, and in which is shown by way of illustration specific embodiments in which the invention may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting unless otherwise specified. It is to be understood that other embodiments may be utilized and structural or logical changes may be made without departing from the scope of the present invention. The following detailed description, therefore, is not to be taken in a limiting sense, and the scope of the present invention is defined by the attached claims.

It is to be understood that the features of the various exemplary embodiments described herein may be combined with each other, unless specifically noted otherwise.

The term "proximal" in this application means that part that is situated next to or near the point of attachment or origin or a central point; for example, as located toward a center of the human body. The prostate is proximal relative to skin of the patient.

The term "distal" in this application means that part that is situated away from the point of attachment or origin or the central point; for example, as located away from the center of the human body. The glans penis is distal relative to the crus penis of the patient.

End means endmost. A distal end is the furthest endmost location of a distal portion of a thing being described, whereas a proximal end is the nearest endmost location of a proximal portion of the thing being described. The portion next to or adjacent to an end is an end portion. For example, a twelve inch ruler has a center point at six inches, a first end at zero inches and a second, opposite end at twelve inches, an end portion adjacent to the first end and another end portion adjacent to the second end.

Embodiments provide an implantable penile prosthetic insert configured to be placed in a corpora cavernosum of a penis. The insert includes a body formed of a bio-compatible material extending between a proximal end and a distal end and having an exterior surface defining a channel extending longitudinally along at least part of the body. The body is configured to transition between a first state corresponding to a flaccid state of the penis and a second state corresponding to the erect state of the penis. The channel is present in both the first and the second state. Providing a channel in the exterior surface of the body is useful to provide room or space in the corpora cavernosum for tissue that desirably remains vascularized or revascularizes following implantation of the insert. Embodiments provide an implantable penile prosthetic insert wherein the channel is more resistant to deformation than a surrounding portion of the body.

Embodiments provide a penile prosthetic system including an inflatable cylinder, a reservoir for storing of liquid and a pump connected between the reservoir and the cylinder via tubing.

Embodiments provide a method of implanting a penile prosthetic in a patient providing for less dilation of healthy penile tissue and thereby increase the quality of the erection.

Embodiments provide a method of implanting a penile prosthetic in a patient wherein the channel is defined by a reinforcing wall having a greater rigidity than a surrounding portion of the body.

Embodiments provide a kit of parts including a packaging, an insert positioning tool, a set of instructions for use and an implantable penile prosthetic insert configured to be placed in a corpora cavernosum of a penis and to transition the penis between a flaccid and an erect state.

FIG. 1 is a cross-sectional view of a penis P. The penis P has been "flipped back" to recline against the abdomen, which is an orientation employed by surgeons for access to the proximal and distal reaches of the penis P. The surgeon gains access to the corpora cavernosa though small incisions, and with this in mind, the cross-sectional view of FIG. 1 is not the view observed by the surgeon. In the view of FIG. 1 the penis P of the patient is reclined against the torso such that the urethra U, surrounded by corpus spongiosum tissue, is oriented upward.

In preparation for the implantation of the penile prosthesis, the groin area of the patient is shaved, cleaned and suitably prepped with a surgical solution prior to draping with a sterile drape as directed by the healthcare provider's procedures. A retraction device, such as a retractor sold under the trademark Lone Star and available from Lone Star Medical Products of Stafford, Tex. is placed around the penis P. A catheter is inserted into the urethra U from the distal end of the penis P into the bladder. Thereafter, the surgeon forms an incision to access the corpora cavernosa C1 and C2 of the penis.

Suitable examples of incisions include either an infrapubic incision or a transverse scrotal incision. The infrapubic incision is initiated between the umbilicus and the penis (i.e., above the penis), whereas the transverse scrotal incision is made across an upper portion of the patient's scrotum.

In the transverse scrotal approach the surgeon forms a 2-3 cm transverse incision through the subcutaneous tissue of the median raphe of the upper scrotum and dissects down through the Darto's fascia Df and Buck's fascia Bf to expose the tunicae albuginea TA of the penis P. Thereafter, each corpora cavernosum C1 and C2 is exposed in a corporotomy where a small (approximately 1.5 cm) incision is formed to allow the surgeon to access to the corpora cavernosa C1 and C2.

In a typical approach, one or both of the corpora cavernosum C1, C2 is dilated with an appropriate dilation tool to form a recess in the penis P that is sized to receive an insert, e.g. a cylinder. A dilation tool including length indicia is inserted into the dilated corpora cavernosum C1, C2 to measure the length of the corpora prior to selecting an appropriately sized insert. The dilation tool is removed from the penis P.

In some cases, patients suffering from erectile dysfunction have some, or even a majority of healthy tissue left in the corpora cavernosum but are unable to get an erection due to other reasons. It is beneficial to the patient and his sexual partner if as little as possible of healthy tissue of the corpora cavernosum is dilated away prior to placement of an implant, for at least the reason that the healthy tissue that remains will allow the penis to remain warm to the touch. Having some remaining vascularized tissue inside the corpora cavernosum, even with a penile prosthetic implanted in the corpora cavernosum, helps provide for a better (harder, bigger) as well as a more naturally feeling erection because better or more flow of warm blood provides warming of the surrounding penile tissue. Particularly advantageous is improved flow of warm blood to the tissue of, or adjacent to, the penis glans.

FIG. 2A is a top-view of one embodiment of an implantable penile prosthetic insert (PPI) 20 configured to be placed in a corpora cavernosum C1, C2 of a penis P. In one embodiment, the PPI 20 includes a body 22 formed of a bio-compatible material and extends between a proximal end 24 and a distal end 26. In one embodiment, the body 22 includes an exterior surface 28 that defines a channel 30 extending longitudinally along at least part of the body 22. In one embodiment, the body 22 is configured to transition between a first state corresponding to a flaccid state of the penis and a second state corresponding to an erect state of the penis. In the erect state the insert has a column strength that is selected to be sufficient to permit penetration associated with intercourse. In one embodiment, the channel 30 is more resistant to deformation than a surrounding portion of the body 22. In one embodiment, for example, the channel 30 is more resistant to deformation such that the channel 30 is present in both the first and in the second state. Embodiments achieving a higher resistance to deformation of the channel in relation to a surrounding portion of the body 22 include but are not limited to differentiating materials, differentiating thicknesses of materials, differentiating elasticity modules and incorporating one or more layers of other materials and structure between the channel 30 and the surrounding portion of the body 22. In this disclosure, the wording "present" in relation to the channel 30 in both states means that the channel does not go away even if a surrounding portion of the body 22 is deformed. In one embodiment, a cross-section of the channel 30 stays the same in both states. In one embodiment, a cross-section of the channel may change when the body 22 transitions between the first and the second states, but the channel does not lose its functionality. FIG. 2B is a cross-sectional view of the body 22 including the channel 30 of FIG. 2A.

In one embodiment, the channel 30 in the body 22 of the PPI 20 provides room or a space for healthy penile tissue to locate therein. The channel 30 provides an opportunity for the surgeon to minimally dilate the corpora cavernosum, thereby providing room for some vascularized tissue to remain in the corpora to transport blood while simultaneously providing implantation of a PPI 20. In one embodiment, the channel is sized to allow penile tissue to dwell in the channel with sufficient vascularization of the dwelling penile tissue when the PPI 20 is implanted in the penis.

Figure 3A:
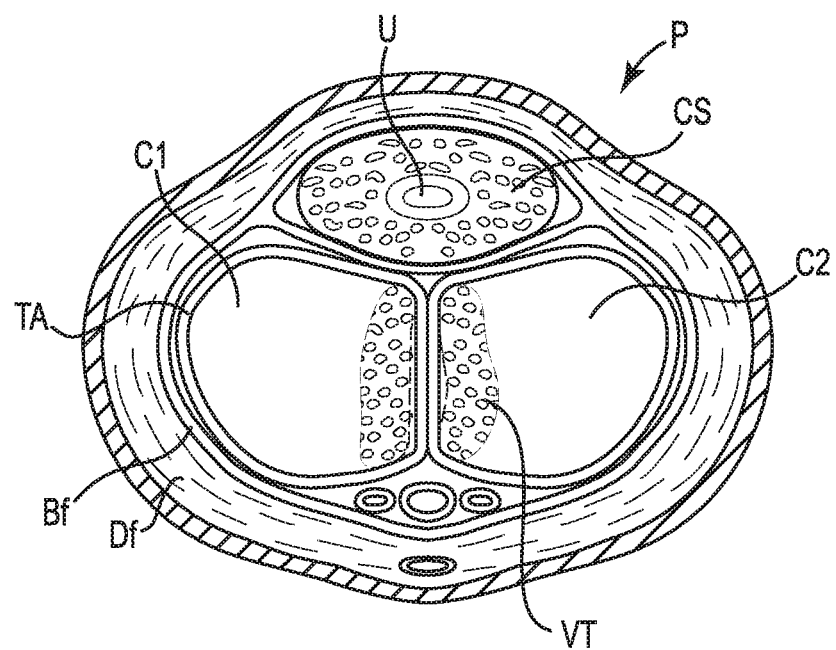
FIG. 3A is a cross-sectional view of a penis P wherein some tissue of the corpora cavernosum has been dilated away while a portion of vascularized tissue remains in the corpora cavernosum.

FIG. 3A is a cross-sectional view of a penis P similar to FIG. 1 in which some, but not all of the spongiosis tissue of the corpora cavernosa C1, C2, has been dilated away thereby leaving a recess for placement of a penile prosthetic, but also leaving some healthy vascularized tissue VT in the corpora C1, C2 to transport blood.

Figure 3B:
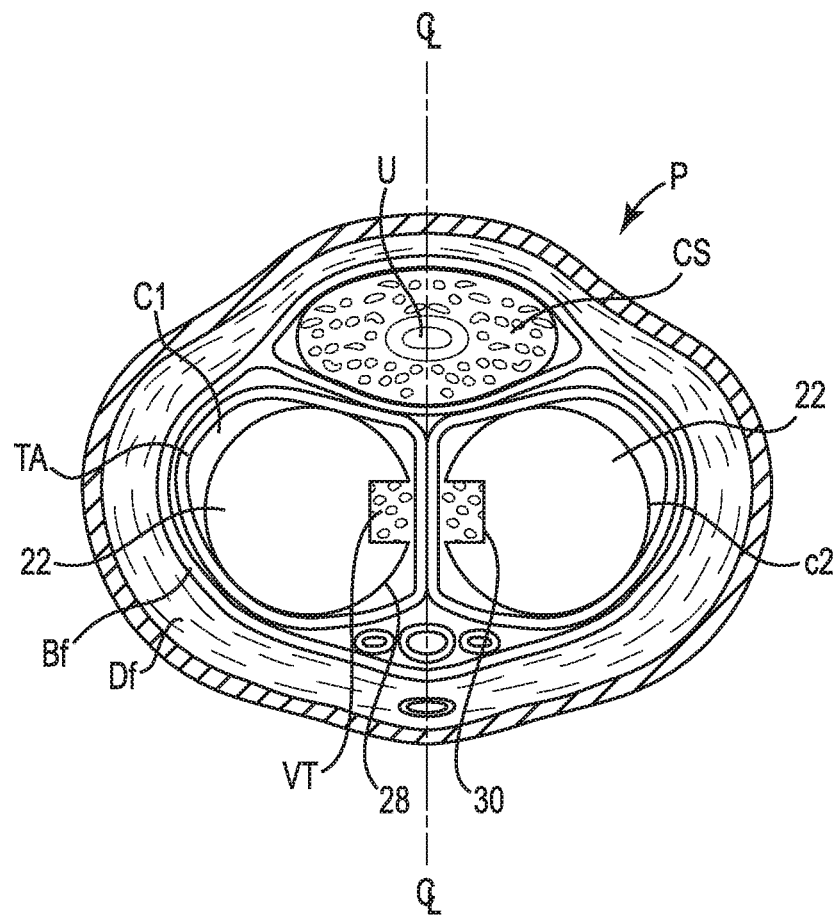
FIG. 3B is another cross-sectional view of a penis P showing an insert located in each of the corpora cavernosum, a channel in the insert accommodating a remaining portion of vascularized tissue located adjacent a midline of the penis.

FIG. 3B is another cross-sectional view of a penis P similar to FIGS. 1 and 3A and showing a body 22 of a PPI 20 located in each corpora cavernosum C1, C2. A longitudinally extending channel 30 is defined in the exterior surface 28 of the body 22 and provides room or space for maintaining some of the vascularized tissue VT in the corpora even after implantation of the PPI 20.

FIG. 4 is a top view showing one embodiment, wherein the PPI 20 includes a rear proximal tip 32 attached to a proximal end portion of the body 22. In one embodiment the PPI 20 includes a front distal tip 34 attached to a distal end portion of the body 22. In one embodiment, the PPI 20 includes an inflatable chamber configured to be inflated by filling the inflatable chamber with inflation fluid to create an erection in the penis. In one embodiment, the rear proximal tip 32 includes a conduit 36 one end of which is in fluid communication with the inflation chamber and another end of which conduit is attachable to a supply of inflation fluid. Among other things, the rear proximal tip 32 is useful for stabilizing the implanted PPI 20 in the crus of the penis. Among other things, the front distal tip 34 is useful for improved filling of the distal end of the corpora cavernosum.

In one embodiment, the channel 30 includes a reinforced sidewall 38 characterized by a greater rigidity of the body 22 along the channel 30. FIG. 5 is a perspective end view of one embodiment of the body 22 wherein the reinforcement of the sidewall 38 includes an increased thickness T of the wall 38 compared to a thickness t of a surrounding portion of the body 22. The increased thickness T of the wall 38 can be obtained through applying subsequent layers of the material used for the body 22 to build up the wall thickness.

Figure 6C:
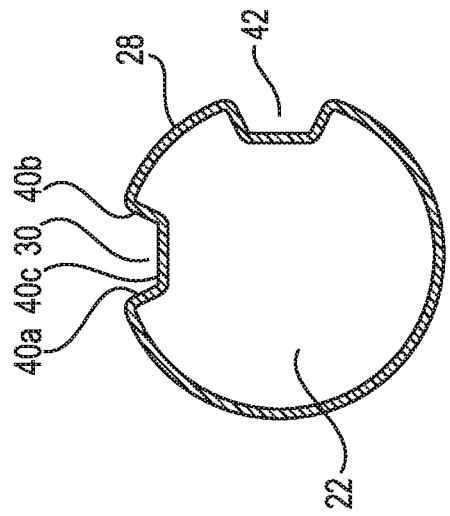
FIGS. 6A-6C are cross-sectional views of different configurations of embodiments of a channel in the body of a penile prosthetic insert.
Figure 6B:
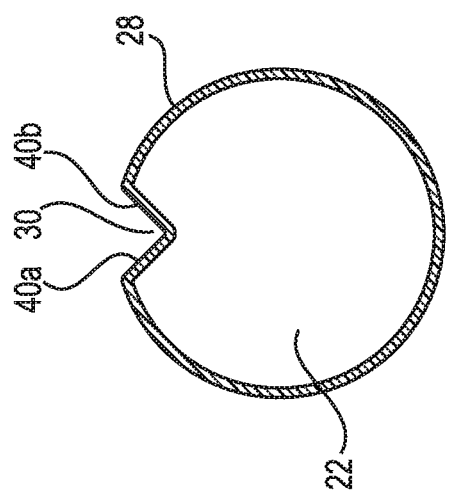
Figure 6A:
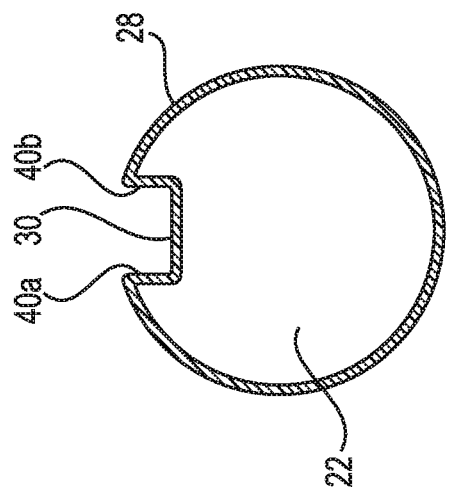

In one embodiment, the channel 30 includes two mutually facing walls 40a, 40b. FIGS. 6A-6C are cross-sectional views of different configurations of a body 22 including a channel 30 and also including two mutually facing sidewalls 40a, 40b. FIG. 6A shows one embodiment of a rectangular shaped cross-section of the channel 30 in which the mutually facing sidewalls 40a, 40b are vertical. FIG. 6B shows one embodiment of a V-shaped cross-section of the channel 30 in which the mutually facing sidewalls 40a, 40b are at an incline. FIG. 6C shows one embodiment of a channel 30 having inclined mutually facing sidewalls 40a, 40b and a third wall 40c. FIG. 6C also shows one embodiment including a second channel 42. More than one channel, i.e. a plurality of channels 30, 42 can be incorporated in the body 22 to further ensure increased vascularization. Other cross-sectional configurations of the channels 30, 42 in the body 22 of the PPI 20 are acceptable. In some embodiments, a cross-sectional area of the channel 30, 42 is 5-50% of a total cross-sectional area of the insert. The dimensions and shape of the channel 30, 42 can be configured to help providing for a differentiation between the channel 30, 42 and the surrounding portion of the body 22 such that the channel 30, 42 is more resistant to deformation than the body.

FIG. 7A is a perspective end view of one embodiment wherein the body 22 includes a reinforcing layer 44 extending along the channel 30. In one embodiment, the reinforcing layer 44 is integrally formed with a wall 40d of the channel 30. In one embodiment, the reinforcing layer 44 is incorporated within the wall 40d as shown in the cross-sectional view of the body 22 in FIG. 7B. In one embodiment, the reinforcing layer is provided as an individual layer attached to the exterior surface 28 of the body 22 by bonding or welding. FIG. 7C is a schematic view of one embodiment of the reinforcing layer 44 including a mesh structure 46. The mesh structure 46 can include polymeric and/or metallic materials.

FIG. 8 is a perspective end view of one embodiment wherein the channel 30 includes a tissue facing surface 48 provided with a tissue ingrowth promoting material 50. Providing a tissue ingrowth promoting material in the channel 30 provides a possibility for increasing the level of vascularized tissue in the channel 30 of the PPI 20 and in the corpora cavernosum by natural ingrowth of tissue, thereby leading to even better flow of blood but also aiding in retaining the body 22 of the PPI 20 stabile in the corpora cavernosum. Suitable tissue ingrowth promoting materials include PGA-Polyglycolide, PLLA—Poly(L-lactic acid), PLGA—Poly(l-lactide-co-glycolide), PLGA-collagen, PEU—Poly(ester urethane) and Collagen.

The body 22 is configured to transition between a first state corresponding to a flaccid state of the penis and a second state corresponding to an erect state of the penis. To achieve this transition, in one embodiment, the PPI 20 includes a malleable shaft.

Figure 9:
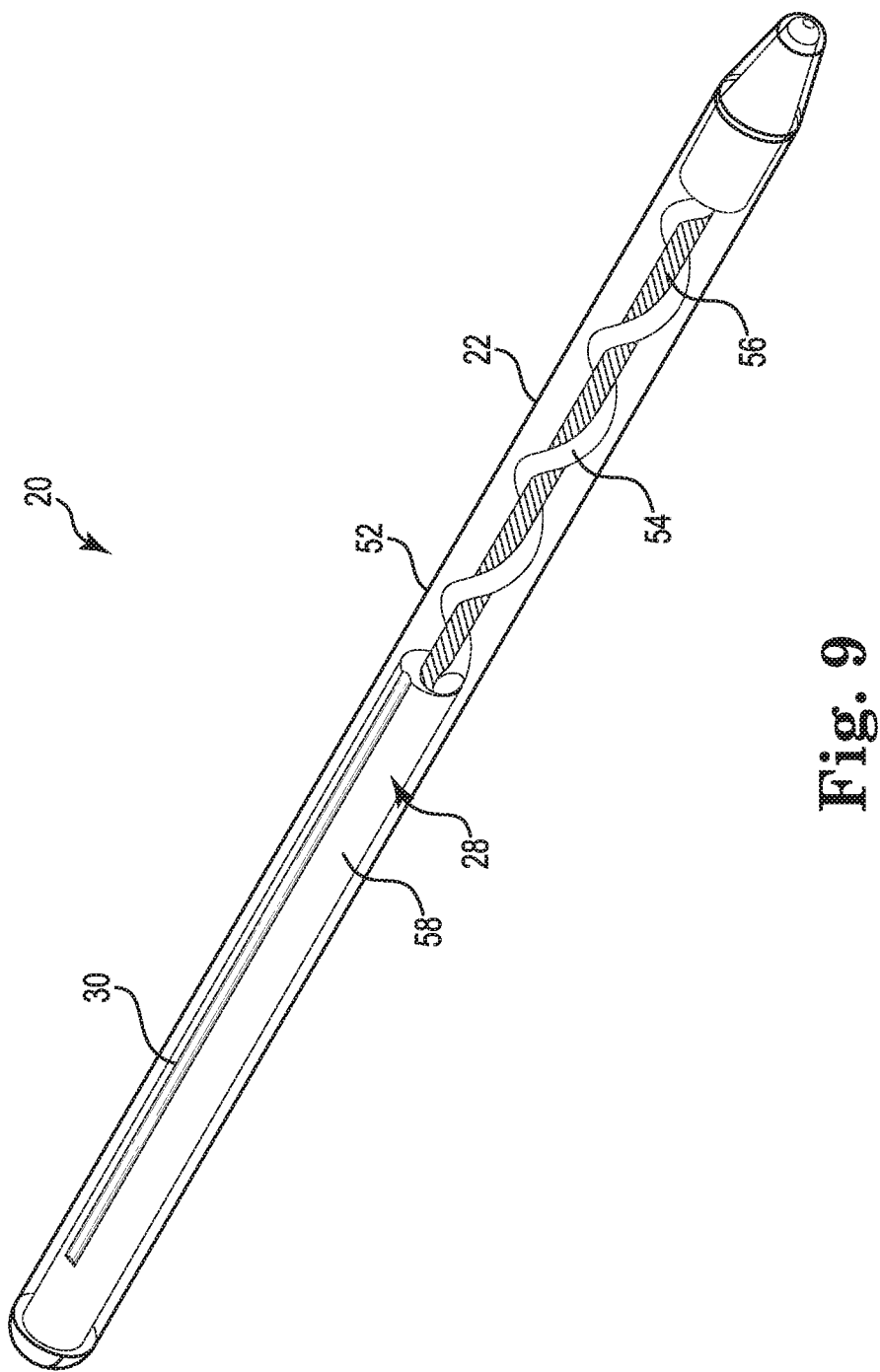
FIG. 9 is a schematic perspective view of one embodiment of an insert including a malleable cylinder.

FIG. 9 is a perspective view of one embodiment wherein the body 22 of the PPI 20 includes a malleable cylinder including a silicone elastomer shaft 52 and a silver wire coil 54 configured to be placed around a silver wire core 56. In one embodiment, a portion of the core and coil is wrapped in a polymer 58 such as urethane and at least one other portion is wrapped in a polymer such as a polyester or a polyethylene terephthalate. In one embodiment, both portions are over-molded with a silicone rubber to form the body 22. In one embodiment, a hydrophilic coating can be applied to the exterior surface of the body 22. In one embodiment, a channel 30 for accommodating vascularized tissue is provided in an exterior surface 28 of the body 22. In one embodiment, the hydrophilic coating can also be in the channel 30. The silver wire coil and core in the cylinder enables the PPI 20 to transition between an erect position (second state) for sexual activity and a lowered flaccid position (first state) for concealment under clothing.

In one embodiment, the transition of the body 22 between the first and the second state is done by inflating/deflating an inflatable chamber of the body 22 with an inflation fluid. The inflatable chamber is configured to be in fluid communication with a fluid reservoir through tubing and a pumping means. The pumping means is configured to be activatable to pump inflation fluid from the reservoir to the inflatable chamber of the body 22 in order for the body 22 to transition from the first flaccid state to the second state. The pumping means can include a deflation valve configured for deflating the inflatable chamber and transition the body 22 back into the first state.

FIG. 10 is a side view of one embodiment, wherein the body 22 of the insert 20 includes an inflatable chamber 35. In one embodiment, the insert 20 includes a rear proximal tip 32 attached to a proximal end portion of the body 22. In one embodiment, tubing 36 extending from the rear proximal tip 32 and being in fluid communication with an inflatable portion of the body 22, extends in a portion of the channel 30. In some embodiments, the channel 30 extends further along the longitudinal extent of the body 22, such as proximally beyond the interface with the rear proximal tip and distally beyond the interface with the front distal tip 34. In the side view of FIG. 10, the channel 30 is shown in phantom line. Configuring the tubing 36 in the channel 30 provides for the penile prosthetic to take up less space in the corpora cavernosum during implantation. This is advantageous in that the inflatable chamber often is somewhat inflated during implantation of the insert. This facilitates an easier insertion of the insert into the corpora for the surgeon and also means that less potentially healthy tissue is dilated away from the corpora when implanting the insert.

FIG. 11A is a side view showing one embodiment wherein a distal end portion 60 of the body 22 includes an engagement feature 62 configured for releasable engagement with an insert positioning tool 64. In one embodiment, the engagement feature 62 includes a ledge 66 overlaying and covering a portion of the channel 30 at the distal end portion 60 of the body 22. FIG. 11B is a top view of the distal end portion 60 of the body 22 indicating the position of the ledge 66. Configuring the engagement feature 62 as ledge 66 allows for the insert positioning tool 64 to be retracted after positioning of the body 22 in the corpora cavernosum with reduced or no probability of unintentionally pulling the body 22 of the PPI 20 back out through the incision.

An insert positioning tool 64 is shown in FIG. 11A. In one embodiment, the tool 64 includes an elongated stem 68 connected to a handle 70 through an intermediate section. In one embodiment, the intermediate section 72 is S-shaped. In one embodiment, the tool 64 includes a straight stem connected to a handle without an intermediate section. As schematically shown in FIG. 11A, the elongated stem 68 is advantageously sized to be positionable in the channel 30 of the body 22 of the PPI 20. When the PPI 20 is to be positioned in the corpora cavernosum the stem 68 locates in the channel 30 and is in engagement with ledge 66 thereby making it possible to move the body 22 distally (forward) towards the penis glans. A distal end portion 74 of the insert positioning tool 64 is configured for engagement with the engagement feature 62 of the body 22. The engagement feature 62 is configured to allow easy engagement and disengagement with the insert positioning tool 64 such that the tool 64 can be easily released from the engagement with the insert 20. As the stem 68 of the insert positioning tool 64 is sized to be accommodated the channel 30, the insert positioning tool 64 is easily retractable "through" the channel 30 and the incision with less risk of damaging healthy tissue. Also, using the insert positioning tool 64 to position and locate the insert 20 in the corpora cavernosum obviates the need for using a needle (sometimes called a "Keith" needle) for the positioning of the insert 20. In a typical procedure, an insert of appropriately selected size length is secured to a suture, and the suture is secured to a needle that is delivered through the dilated corpora cavernosum and out the glans penis where the suture is employed to tow the insert into place within the dilated corpora cavernosum. Using the insert positioning tool 64 instead of a needle and a tow suture attached to the insert helps provide for faster healing times to the benefit of the patient. The channel 30 in the exterior surface 28 of the body 22 helps provide for accommodation of the insert positioning tool 64 and thereby for easier insertion and removal of the tool and insert.

Figure 12:
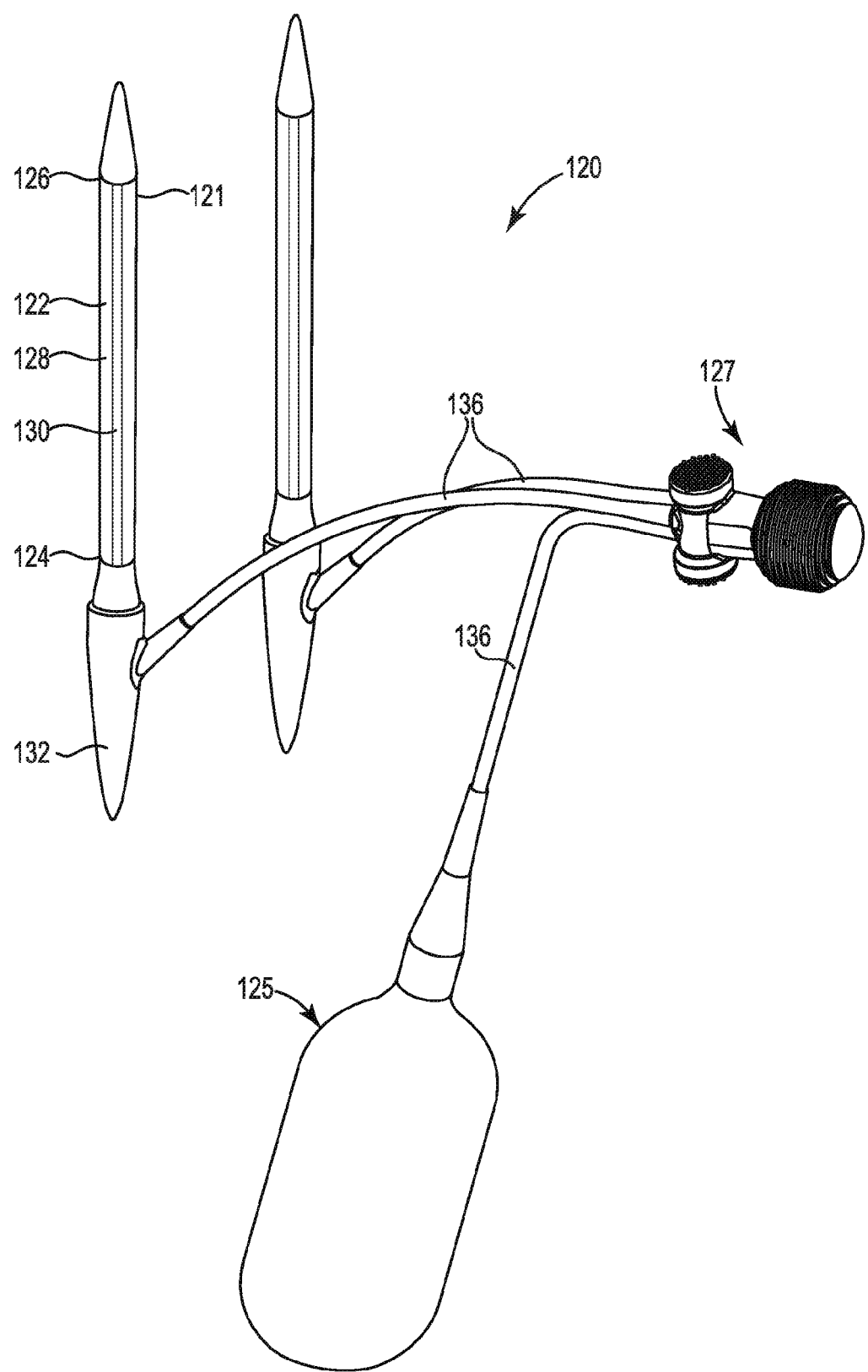
FIG. 12 is a perspective view of one embodiment of a penile prosthetic system.

In one aspect, the disclosure relates to a penile prosthetic system. FIG. 12 is a perspective view of one embodiment of a penile prosthetic system 120 of the application. The system includes an inflatable cylinder 121, a reservoir 125 for storing of liquid and a pump 127. The pump 127 is connected between the reservoir 125 and the cylinder 121 via tubing 136. The pump is configured to move liquid from the reservoir 125 to the cylinder 121 upon activation of the pump by the user. The cylinder 121 includes a body 122 formed of a bio-compatible material extending between a proximal end 124 and a distal end 126 and having an exterior surface 128. A channel 130 is defined in the exterior surface 128 and extends longitudinally along at least part of the body 122. The channel 130 is more resistant to deformation than a surrounding portion of the body 122. The channel 130 provides for accommodation of some healthy tissue in the corpora cavernosum along the implanted cylinder 121 and provides similar advantages as described above for the channel 30 in the penile prosthetic insert 20.

Figure 13:
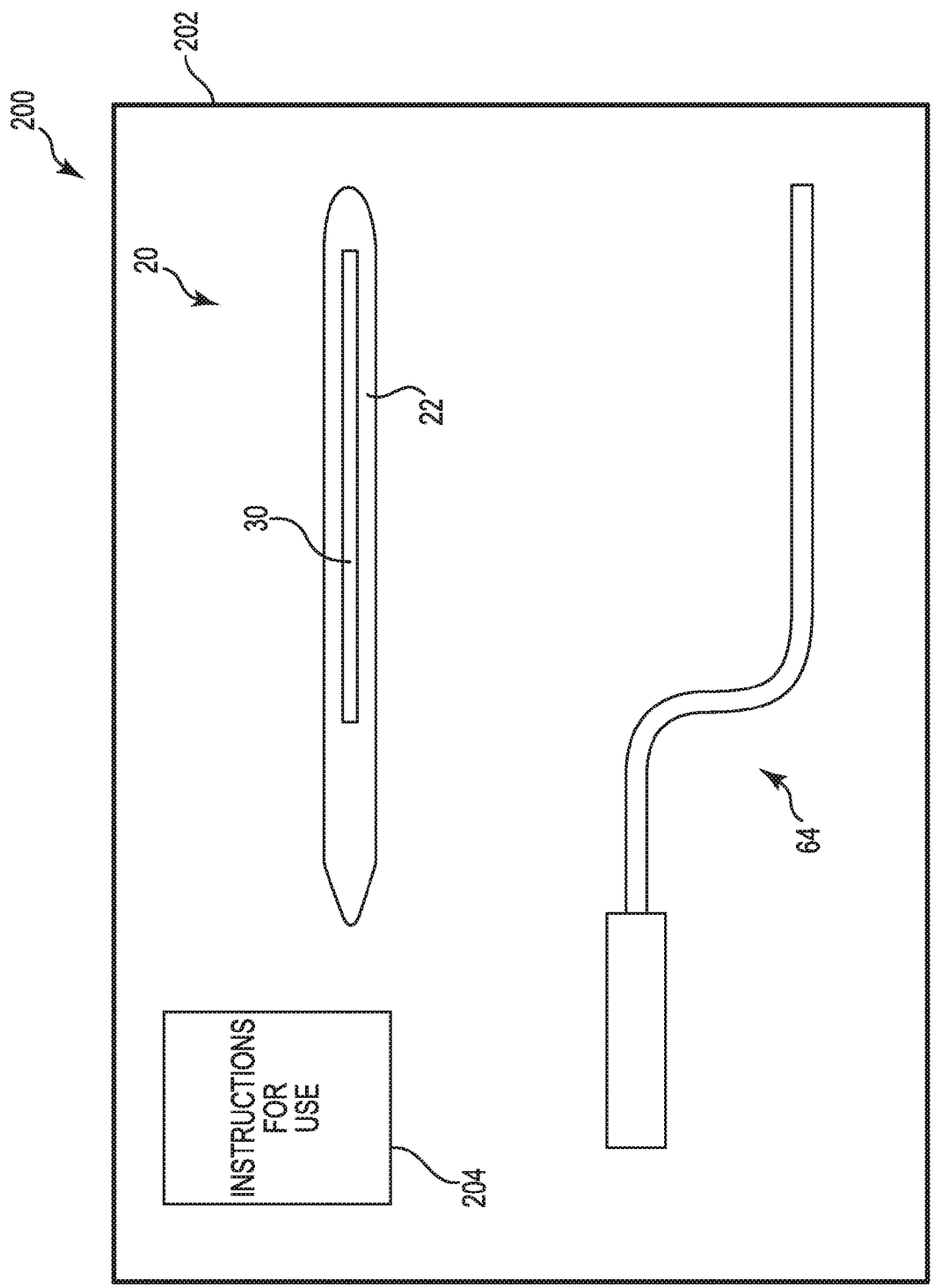
FIG. 13 is a top view of one embodiment of a kit of parts including a penile prosthetic insert having a channel, an insert positioning tool and a set of instructions for use.

In one aspect, the disclosure relates to a kit of parts. FIG. 13 is a top view of a kit of parts 200 of the application including a packaging 202 containing a penile prosthetic insert 20, an insert positioning tool 64 and a set of instructions for use 204. The insert 20 is configured to be placed in a corpora cavernosum of a penis and to transition the penis between a flaccid and an erect state. The insert 20 includes a body formed of a bio-compatible material extending between a proximal end and a distal end and having an exterior surface defining a channel 30 extending longitudinally along at least part of the body. The body 22 is configured to transition between a first state corresponding to the flaccid state of the penis and a second state corresponding to the erect state of the penis. The channel 30 is present in both the first and the second state. In one embodiment, the channel is sized to accommodate at least a portion of the insert positioning tool 64. In one embodiment, the kit of parts 200 includes an insert 20 having a body 22 including an inflatable cylinder. In one embodiment, the kit of parts 200 includes an insert 20 having a body 22 including a malleable cylinder.

In one embodiment, the kit of parts 200 includes a grooved dilator 210 for dilating the corpora cavernosum.

Figure 14B:
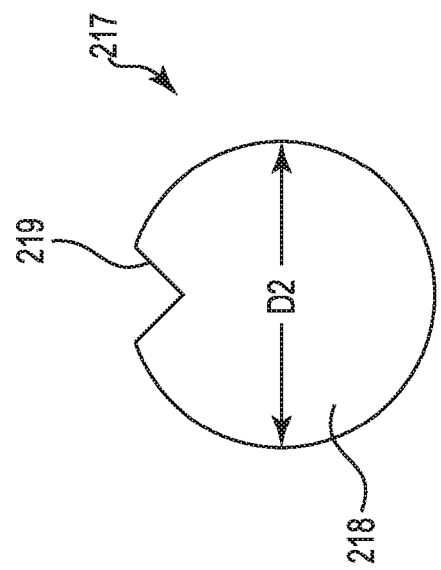
FIG. 14B is a cross-sectional view of the dilation portion of the dilation tool of FIG. 14A.
Figure 14A:
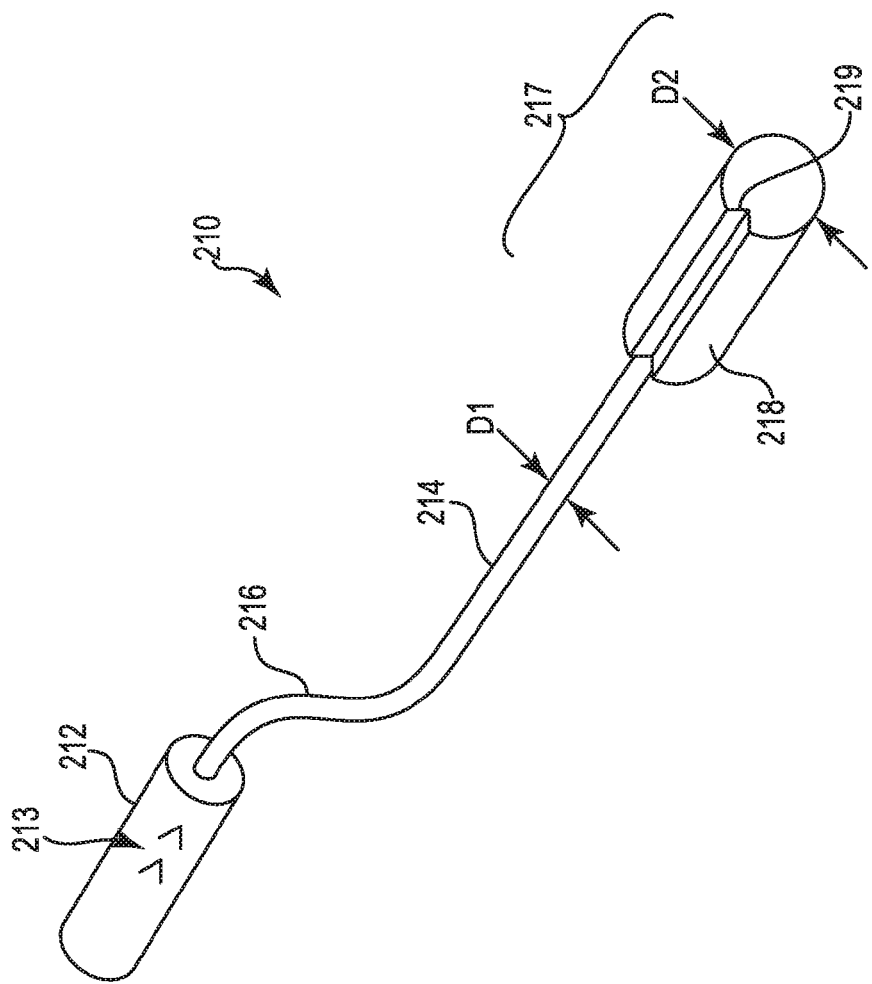
FIG. 14A is a perspective view of one embodiment of a dilation tool having a dilation portion including a groove.

FIG. 14A shows one embodiment, wherein the grooved dilator 210 includes a handle portion 212, and a stem portion 214 connected between the handle portion 212 and a distal end portion 217. In one embodiment, the handle portion 212 and the stem portion 214 are connected via an intermediate section 216. In one embodiment, the intermediate section 216 is S-shaped. A distal end portion 217 of the grooved dilator 210 includes a dilation portion 218 of larger second diameter D2 than a first diameter D1 of the stem portion 214.

In one embodiment, the dilation portion 218 includes a groove 219 or recess in an exterior surface of the dilation portion 218 that is provided to ensure that some of the tissue of the corpora is not dilated, or remains un-dilated when forming a space in the corpora cavernosa for placement of the implant.

The dilation portion 218 of the grooved dilator 210 is configured to leave at least one section or segment of tissue in the corpora undisturbed and un-dilated. The undisturbed tissue remains vascularized (or re-vascularizes) to beneficially warm the penis and aid in effecting an erection. Without being bound to this theory, vascularization of the section of tissue that is left undisturbed is thought to play a role in assisting in achieving an erection and in warming an erect penis. Partners have expressed a desire to have the tip portion of the penis warm after an erection is achieved.

In one embodiment, groove 219 extends along the entire length of the dilation portion 218 (FIG. 14A). In one embodiment, the handle portion 212 includes indicia 213 indicating a corresponding position of the groove 219 in an exterior surface of the dilation portion 218. Alternatively, the indicia 213 can be provided on the stem portion 214 or on both the handle and stem portions. In one embodiment, groove 219 is formed to have a constant groove depth. FIGS. 14C-14D show a perspective view and a side view respectively of one embodiment of the dilation portion 218 (handle 212 and stem 214 of dilator 210 not shown) wherein groove 219 is formed to be deeper along a proximal portion 221 of the dilation portion 218 and shallower along a distal portion 223 of the dilation portion 218. In one embodiment, the exterior surface of the dilation portion 218 defines a plurality of grooves 219 (FIG. 14E). In one embodiment illustrated in FIG. 14B, the groove 219 has a cross-sectional profile corresponding to the channel 30 (such as e.g. that of FIG. 6B) in the exterior surface of the body of the insert. Thereby, the grooved dilator 210 can advantageously be used to dilate the corpora cavernosum prior to the introduction of the PPI 20 having a channel 30 of corresponding profile. In one embodiment, the groove 219 or recess of the grooved dilator 210 is sized to have a cross-sectional profile area that is 5-50% larger than the cross-sectional profile area of the channel 30 in the body 22 of the PPI 20.

In one embodiment, the insert positioning tool 64 and the grooved dilator 210 of the kit of parts 200 are integrated into a single device 222. FIG. 15 is a top view of the device 222. In one embodiment, the device 222 includes a handle portion 224 provided between a positioning portion 226 and a dilating portion 228. In one embodiment, the positioning portion includes a stem 230 and a distal end portion 232 configured to engage with an engagement feature of a PPI 20. In one embodiment, the dilating portion 228 includes a stem 234 and a dilation portion 236 including a groove 238.

In one embodiment, the groove 238 corresponds to a channel 30 in a PPO 20 and can advantageously be used to dilate the corpora cavernosum prior to the introduction of the PPI 20 that is then introduced by using the positioning portion 226 of the device 222 to introduce and correctly locate the insert 20.

The insert includes a body formed of a bio-compatible material. Suitable bio-compatible materials for the body of the insert include silicones, polymers such as urethanes, blends of polymers with urethane, copolymers of urethane and ePTFE.

Figure 16:
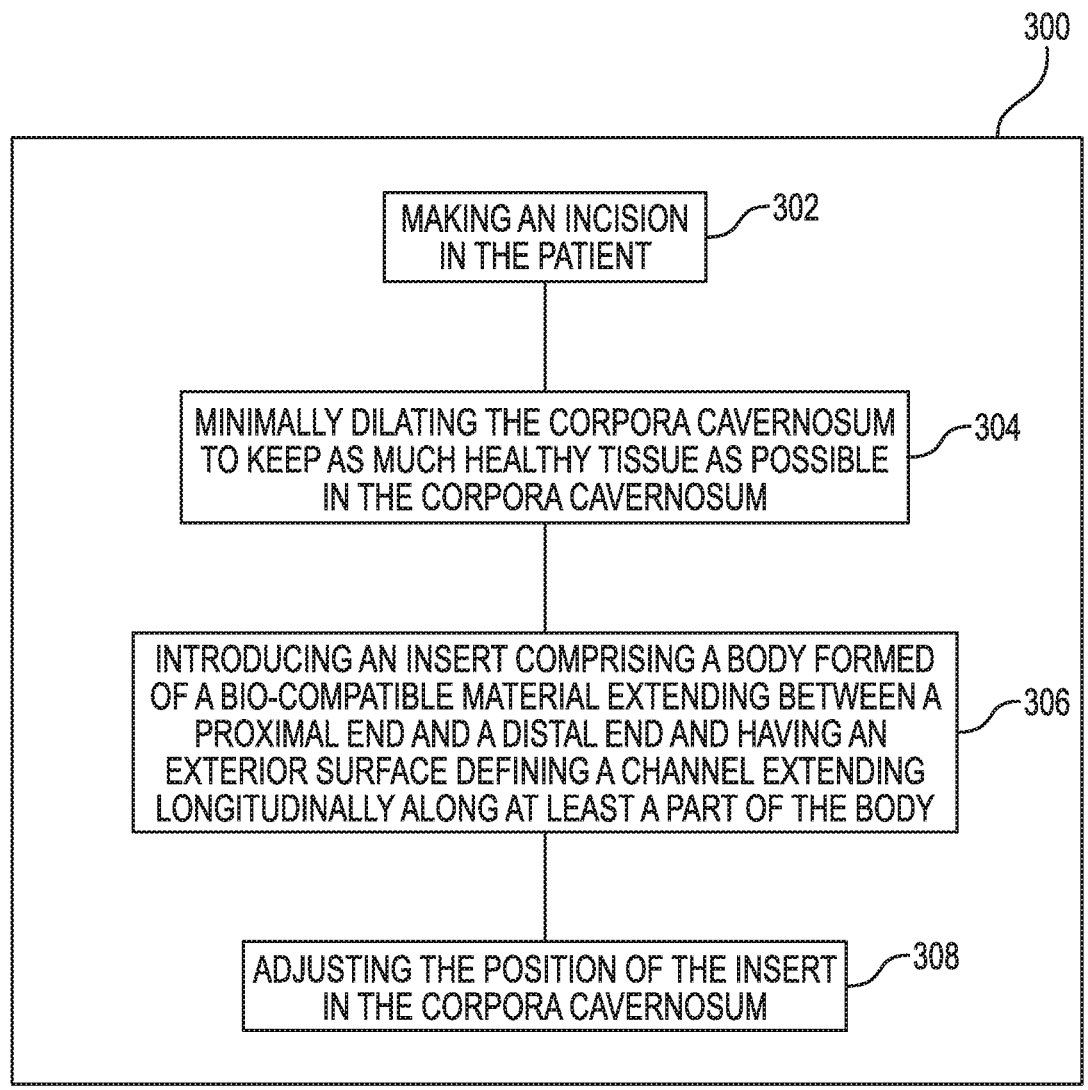
FIGS. 16-18 are block diagrams illustrating embodiments of a method of implanting a penile prosthetic insert in a patient.

In one aspect, the disclosure relates to a method of implanting a penile prosthetic in a patient. FIG. 16 is a block diagram showing one embodiment of the method 300. After having prepared the patient for the surgical procedure in a manner described above, the surgeon at 302 makes an incision in the patient. At 304, the surgeon minimally dilates the corpora cavernosum, thereby making sure to keep (or maintain) as much healthy tissue as possible in the corpora cavernosum. At 306, the surgeon introduces an insert 20 including a body 22 formed of a bio-compatible material extending between a proximal end 24 and a distal end 26 and having an exterior surface 28 defining a channel 30 extending longitudinally along at least a part of the body 22. In one embodiment, the surgeon at 308 adjusts the position of the insert 20 in the corpora cavernosum such that the insert 20 is optimally located. The channel 30 in the exterior surface 28 of the insert 20 provides room or space for the non-dilated remaining tissue inside the corpora cavernosum to dwell in and thereby maintain a supply of warm blood through the healthy tissue, in turn increasing the quality of the erection. At least during introduction of the insert 20 into the corpora cavernosum, the channel 30 in the exterior surface 28 of the body 22 also provides a relief area (or zone) for the healthy tissue that has not been dilated away. The channel 30 in the body 22 of the insert 20 is useful in the method of implanting the penile prosthetic also for the reason that it provides for less of the healthy tissue to be removed thereby saving time used to dilate the corpora. The step of minimally dilating the corpora cavernosum can advantageously be carried out using a grooved dilator having a groove with a cross-sectional profile corresponding to the cross-sectional profile of the channel of the body of the insert to be implanted. Thereby, the grooved dilator prepares the way for the corresponding profile of the body of the insert.

Figure 17:
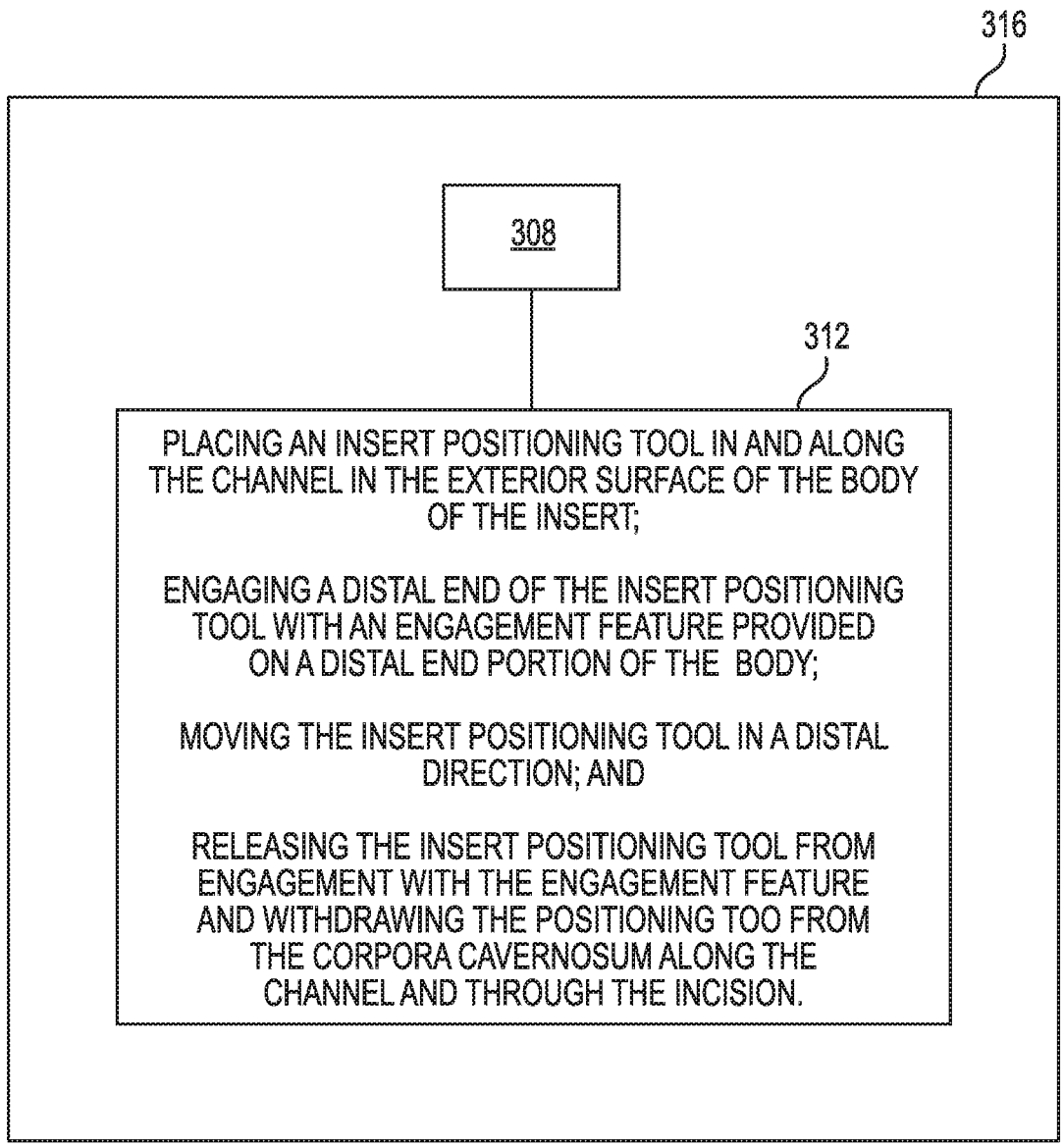

FIG. 17 is a block diagram showing one embodiment 310, wherein the adjusting the position of the insert in the corpora cavernosum 308 includes at 312 placing an insert positioning tool 64 in and along the channel 30 in the exterior surface 28 of the body 22 of the insert 20. In one embodiment, the adjusting of the position includes engaging a distal end of the insert positioning tool 64 with an engagement feature 62 provided on a distal end portion of the body 22. The adjusting of the position includes moving the insert positioning tool 64 in a distal direction. Thereby the insert 20 is pushed forward into the corpora cavernosum such that the distal end portion of the body 22 locates at a distal end of the corpora closest to the penis glans. In one embodiment, the adjusting of the position includes releasing the insert positioning tool 64 from engagement with the engagement feature 62 and withdrawing the insert positioning tool 64 from the corpora cavernosum along the channel 30 and out through the incision in the patient. Withdrawal of the tool 64 via the channel 30 in the insert 20 provides a reduced or eliminated probability of interfering with healthy tissue during retraction of the positioning tool. As the insert positioning tool 64 can further be releasably engaged with the insert 20, any chance of unintentionally withdrawing the implanted insert 20 back out through the incision during removal of the tool 64 is also greatly reduced or eliminated.

Figure 18:
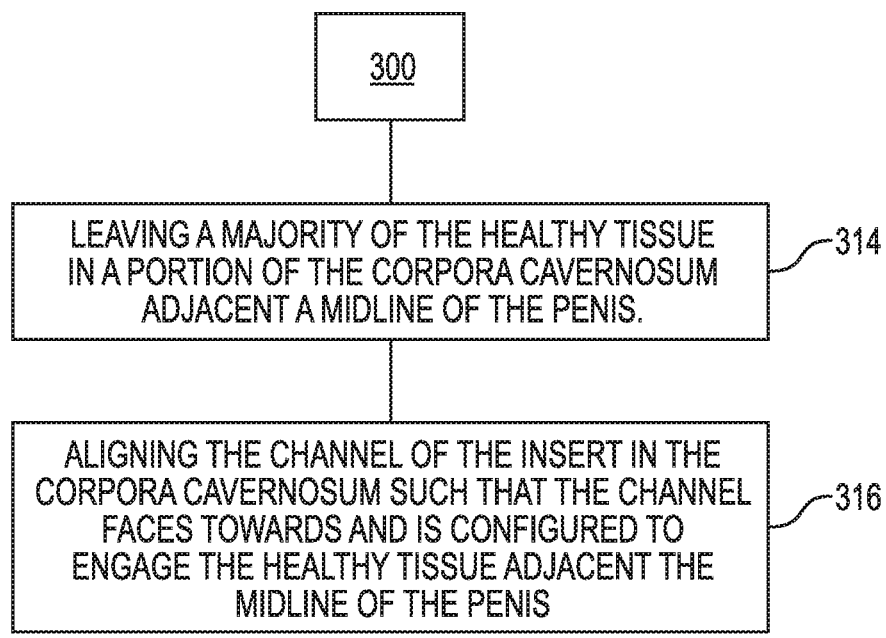

FIG. 18 is a block diagram showing one embodiment 314, wherein the method includes leaving a majority of the healthy tissue in a portion of the corpora cavernosum adjacent a midline of the penis (see also FIG. 3A).

In another embodiment 316, the method includes aligning the channel of the insert in the corpora cavernosum such that the channel faces towards and is configured to engage the healthy tissue adjacent the midline of the penis.

Leaving a majority of the healthy tissue in the corpora adjacent a midline of the penis and aligning the channel of the insert to face towards that tissue ensures that the patient does not experience an undesirable unevenness of the surface of the penis during an erection. Also, keeping the healthy tissue adjacent the midline is believed to provide the best conditions for improved vascular flow and thereby supply of warm blood towards the penis glans. In other embodiments, the majority of healthy tissue could include portions of tissue along a part or an entire periphery of the corpora cavernosum. In one embodiment, a PPI 20 could be located in a corpora cavernosum such that it is encircled by healthy tissue. Depending on individual patient needs, different tissue areas or zones may be particularly desirable to keep for achieving an optimal erection.

Embodiments provide an improved penile prosthetic insert and a method for implantation of the insert for treating erectile dysfunction. The penile prosthetic insert described in this disclosure helps provide for a larger portion of healthy vascularized tissue to remain in the corpora cavernosum of a penis thereby leading to increased quality of the erection. Also, the channel in the exterior surface of the body of insert helps provide for accommodating an insert positioning tool during incorporation and adjusting of the position of the insert in the penis and retracting the tool with little or no probability of unintentionally withdrawing the insert. The insert positioning tool obviates use of a needle and a tow suture attached to the insert for positioning the insert in the corpora cavernosum and helps provide for reduced trauma to penile tissue and thereby to faster healing times to the benefit of the patient.

Although specific embodiments have been illustrated and described, it will be appreciated by those of ordinary skill in the art that a variety of alternate and equivalent implementations may be substituted for the specific embodiments shown and described without departing from the scope of the present invention. This application is intended to cover any adaptations or variations of the kind of medical devices described above. Therefore, it is intended that this invention be limited only by the claims and their equivalents.

What is claimed is:

1. A method of implanting a prosthetic in a penis, the method comprising:
    making an incision in the penis and accessing a corpora cavernosum of the penis;
    inserting a dilator through the incision and into the corpora cavernosum, where the dilator has a handle attached to a stem and a dilation portion attached to a distal end of the stem, where an exterior surface of the dilation portion includes a groove;
    moving the dilation portion of the dilator in a distal direction and in a proximal direction within the corpora cavernosum and dilating a first portion of tissue in the corpora cavernosum;
    orienting the groove formed in the dilation portion of the dilator relative to the penis and leaving a second portion of the tissue in the corpora cavernosum within the groove un-dilated;
    implanting a penile prosthetic into the corpora cavernosum, where an exterior surface of the penile prosthetic is formed to include a channel; and
    aligning the channel formed in the penile prosthetic into engagement with the second grooved portion of the tissue in the corpora cavernosum.

2. The method of claim 1, where orienting the groove formed in the dilation portion of the dilator relative to the penis includes orienting the groove formed in the dilation portion of the dilator relative to the penis to leave the second portion of the tissue on a midline within the corpoa cavernosum.

3. The method of claim 1, where orienting the groove formed in the dilation portion of the dilator relative to the penis includes orienting the groove formed in the dilation portion of the dilator relative to the penis to leave the second portion of the tissue in the corpoa cavernosum within the groove vascularized.

4. The method of claim 1, where orienting the groove formed in the dilation portion of the dilator relative to the penis includes orienting the groove formed in the dilation portion of the dilator relative to the penis to leave the second portion of the tissue in the corpoa cavernosum within the groove vascularized and thus aiding in warming the penis with an implanted penile prosthetic.

5. The method of claim 1, where the penile prosthetic includes an inflatable penile prosthetic.

6. The method of claim 1, where the penile prosthetic includes a malleable penile prosthetic.

7. The method of claim 1, where the exterior surface of the dilation portion includes a plurality of grooves, and the method further comprising:
    leaving a grooved portion of the tissue in the corpoa cavernosum within each of the plurality of grooves un-dilated.

8. The method of claim 1, where the handle includes indicia, where orienting the groove formed in the dilation portion of the dilator relative to the penis includes
    determining a corresponding position of the groove in the exterior surface of the dilation portion by looking at the indicia on the handle.

9. The method of claim 1, where the stem includes indicia, where orienting the groove formed in the dilation portion of the dilator relative to the penis includes
    determining a corresponding position of the groove in the exterior surface of the dilation portion by looking at the indicia on the stem.

10. The method of claim 1, where the exterior surface of the dilation portion includes the groove, and the groove has a constant depth, where leaving the second portion of the tissue in the corpora cavernosum within the groove un-dilated includes leaving a constant depth grooved portion of the tissue in the corpora cavernosum un-dilated.

11. The method of claim 1, comprising maintaining an orientation of the groove formed in the dilation portion of the dilator relative to the penis such that leaving the second portion of the tissue in the corpora cavernosum within the groove un-dilated includes leaving a linear portion of the tissue in the corpoa cavernosum within the groove un-dilated.

12. A method of implanting a prosthetic in a penis, the method comprising:

making an incision in the penis and accessing a corpoa cavernosum of the penis;

inserting a dilator through the incision and into the corpoa cavernosum, where the dilator has a handle attached to a stem and a dilation portion attached to a distal end of the stem, where an exterior surface of the dilation portion includes a groove;

moving the dilation portion of the dilator in a distal direction and in a proximal direction within the corpoa cavernosum and removing a first portion of vascularized tissue in the corpoa cavernosum;

orienting the groove formed in the dilation portion of the dilator relative to the penis and leaving a second portion of the tissue in the corpoa cavernosum within the groove vascularized;

implanting a penile prosthetic into the corpoa cavernosum, where an exterior surface of the penile prosthetic is formed to include a channel; and aligning the channel formed in the penile prosthetic into engagement with the second portion of the tissue in the corpoa cavernosum that is vascularized.

13. The method of claim 12, where orienting the groove formed in the dilation portion of the dilator relative to the penis includes orienting the groove formed in the dilation portion of the dilator relative to the penis to leave the second portion of the tissue on a midline within the corpoa cavernosum.

14. The method of claim 12, where the penile prosthetic includes an inflatable penile prosthetic.

15. The method of claim 12, where the penile prosthetic includes a malleable penile prosthetic.

16. The method of claim 12, where the exterior surface of the dilation portion includes a plurality of grooves, and the method further comprising:

leaving a grooved portion of the tissue in the corpoa cavernosum within each of the plurality of grooves un-dilated.

17. The method of claim 12, where the handle includes indicia, where orienting the groove formed in the dilation portion of the dilator relative to the penis includes determining a corresponding position of the groove in the exterior surface of the dilation portion by looking at the indicia on the handle.

18. The method of claim 12, where the stem includes indicia, where orienting the groove formed in the dilation portion of the dilator relative to the penis includes determining a corresponding position of the groove in the exterior surface of the dilation portion by looking at the indicia on the stem.

19. The method of claim 12, comprising maintaining an orientation of the groove formed in the dilation portion of the dilator relative to the penis such that leaving the second portion of the tissue in the corpora cavernosum within the groove un-dilated includes leaving a linear portion of the tissue in the corpoa cavernosum within the groove un-dilated.

* * * * *

UNITED STATES PATENT AND TRADEMARK OFFICE
CERTIFICATE OF CORRECTION

PATENT NO. : 9,878,136 B2
APPLICATION NO. : 15/446016
DATED : January 30, 2018
INVENTOR(S) : Jeffrey Brian Taylor Page 1 of 1

It is certified that error appears in the above-identified patent and that said Letters Patent is hereby corrected as shown below:

In the Claims

Claim 1 at Column 12, Line 9:
"with the second grooved portion"
Should read:
"with the second portion"

Signed and Sealed this
Twenty-first Day of August, 2018

Andrei Iancu
*Director of the United States Patent and Trademark Office*